US00RE42933E

(19) United States
(12) Reissued Patent
Tang et al.

(10) Patent Number: US RE42,933 E
(45) Date of Reissued Patent: Nov. 15, 2011

(54) METHOD AND APPARATUS FOR AVOIDING UNWANTED SENSING IN A CARDIAC RHYTHM MANAGEMENT DEVICE

(75) Inventors: Zhengnian Tang, Shoreview, MN (US); Julio C. Spinelli, Lakewood Ranch, FL (US); Jeffrey E. Stahmann, Ramsey, MN (US); Rene H. Wentkowski, Berlin (DE); Andrew P. Kramer, Marine on St. Croix, MN (US); Paul A. Haefner, Circle Pines, MN (US)

(73) Assignee: Cardiac Pacemakers, Inc., St. Paul, MN (US)

(21) Appl. No.: 11/900,901

(22) Filed: Sep. 13, 2007

Related U.S. Patent Documents

Reissue of:
(64) Patent No.: 6,944,499
Issued: Sep. 13, 2005
Appl. No.: 10/066,989
Filed: Feb. 4, 2002

(51) Int. Cl.
*A61N 1/00* (2006.01)
(52) U.S. Cl. ..... 607/9
(58) Field of Classification Search ..... 600/508, 600/510, 518; 607/9, 14, 17, 27, 30, 5
See application file for complete search history.

(56) References Cited

U.S. PATENT DOCUMENTS

| | | | | |
|---|---|---|---|---|
| 5,275,621 | A * | 1/1994 | Mehra | 607/5 |
| 5,400,796 | A * | 3/1995 | Wecke | 600/518 |
| 5,470,342 | A * | 11/1995 | Mann et al. | 607/5 |
| 5,643,326 | A * | 7/1997 | Weiner et al. | 607/14 |
| 5,735,881 | A * | 4/1998 | Routh et al. | 607/14 |
| 6,337,996 | B1 * | 1/2002 | Legay et al. | 607/9 |

FOREIGN PATENT DOCUMENTS

| | | |
|---|---|---|
| EP | 0318304 A2 | 5/1989 |
| EP | 0562237 A1 | 9/1993 |
| EP | 0594957 A1 | 5/1994 |
| EP | 0705620 A2 | 4/1996 |

* cited by examiner

*Primary Examiner* — George Manuel
*Assistant Examiner* — Robert N Wieland
(74) *Attorney, Agent, or Firm* — Schwegman, Lundberg & Woessner, P.A.

(57) ABSTRACT

A cardiac rhythm management device that utilizes blanking or refractory periods to avoid misidentification of artifacts and evoked potentials, wherein the refractory periods are discontinuous and may be dependent upon sensed events, expiration of a predefined timing interval, or stimulation events in the same or other chambers of the heart. The discontinuous refractory periods enhance the ability of the device to sense intrinsic events. The present invention includes separate refractory and floating refractory periods incorporated within the sensing protocol for each selected cycle, thereby increasing the time period for normal sensing.

70 Claims, 4 Drawing Sheets

METHOD AND APPARATUS FOR AVOIDING UNWANTED SENSING IN A CARDIAC RHYTHM MANAGEMENT DEVICE

Matter enclosed in heavy brackets [ ] appears in the original patent but forms no part of this reissue specification; matter printed in italics indicates the additions made by reissue.

BACKGROUND OF THE INVENTION

I. Field of the Invention

This invention relates generally to a cardiac rhythm management device suitable for delivering stimulation pulses to a patient's heart and more particularly relates to a cardiac rhythm management device that utilizes a sensing protocol which avoids misidentification of artifacts and evoked potentials enhancing the ability of the device to sense intrinsic events.

II. Discussion of the Prior Art

Over the years, cardiac rhythm management devices have been utilized for supplanting some or all of an abnormal heart's natural pacing functions. These devices have remedied abnormalities including total or partial heart block, arrhythmias, congestive heart failure, congestive heart disorders and other various rhythm disturbances within the heart. Typically, the rhythm management device includes a power supply and pulse generator for generating electrical stimulus pulses delivered to a pre-selected area of the heart. An electrode lead arrangement (either uni-polar or bi-polar) positioned adjacent or within a pre-selected heart chamber is electrically coupled to the pulse generator for delivering stimulation pulses to the desired chamber. More recently, electrode lead arrangements have included multiple electrode leads positioned within a single chamber of the heart.

Regardless of the type of stimulation device employed to restore the heart's natural rhythm (i.e. defibrillators, Congestive Heart Failure (CHF) devices or other devices having logic and timing dependent on sensing of intrinsic heart events), each type operates to stimulate excitable heart tissue cells, which may or may not result in evoked response by the heart. Myocardial evoked response to stimulation or "capture" is a function of the positive and negative charges found in each myocardial cell within the heart. The selective permeability of each myocardial cell works to retain potassium and exclude sodium such that, when the cell is at rest, the concentration of sodium ions outside of the cell membrane are significantly greater than the concentration of sodium ions inside the cell membrane, while the concentration of potassium ions outside the cell membrane are significantly less than the concentration of potassium ions inside the cell membrane. When a stimulus is applied to the cell membrane, the selective permeability of the cell membrane is disturbed and no longer blocks the in-flow of sodium ions from outside the cell membrane. The in-flow of sodium ions at the stimulation site causes the adjacent portions of the cell membrane to lose its selective permeability, thereby causing a chain reaction across the cell membrane until the cell interior is flooded with sodium ions. This process, referred to as "depolarization", causes the myocardial cell to have a net positive charge due to the in-flow of sodium ions and an out-flow of potassium ions. The success of a pacing stimulus in depolarizing or "capturing" the selected chamber of the heart is dependent upon whether the amplitude and/or duration of the stimulus as delivered to the myocardium exceeds a required threshold.

The effective delivery of stimulation pulses is further dependent upon the normal pacing cycle of the heart. The delivery of the stimulation pulse must be delivered at a proper time during the cardiac cycle or the stimulation pulse may not be effective, may not be as effective, or may be undesirable. The determination of the proper timing of the delivery of the stimulation pulse is further dependent upon proper detection of intrinsic activity in the heart. Polarization voltages and after potentials, which develop at the heart tissue electrode interface following the application of a stimulation pulse, affects the ability of the rhythm management device to accurately detect intrinsic activity. As pacemakers have evolved, the pacing modes and configurations have become more intricate and complex, generating an increasing array of polarization voltages and after potentials. Blanking or refractory periods, which may be considered as a means for avoiding unwanted sensing in the cardiac rhythm management devices, are frequently used to prevent artifacts and after potentials from being improperly detected as intrinsic events. Such blanking or refractory periods are typically initiated upon sensing an intrinsic activity or delivering a stimulation pulse and last until the end of all predictable artifacts and evoked potentials associated with the event. The blanking or refractory period, in effect, causes the pacing logic of the device to "ignore", for example, detected intrinsic activity. Thus, the typical cardiac rhythm management device runs "blind" even if there is a period of time during this preset period for which no artifact or evoked potential is present and response to a detected intrinsic activity may be desirable.

For example, when pacing in the ventricles and sensing in the atrium, an atrial channel of a sensing circuit of the present day cardiac rhythm management devices may have to be refractory most of the time because of a long retrograde conduction time. Consequently, a P-wave resulting from intrinsic depolarization may easily fall into a refractory or blanking period, in which case the intrinsic atrial events will not be detected by the device. This reduces the effectiveness of the stimulation protocol of the device. U.S. Pat. No. 5,735,881 to Andre Routh et al. provides a method for increased sensing of intrinsic depolarizations by bifurcating the blanking period with an atrial sensing period. The Routh et al patent teaches the use of a fixed blanking period during the post ventricular atrial refractory period (PVARP) and a programmable blanking period to prevent the mischaracterization of a far field R-wave as an atrial depolarization event. However, the Routh et al patent does not teach or suggest a method for accounting for the complex polarization voltages and after potentials generated by multiple site pacing. Multiple site pacing may include at least one pacing/sensing site in an atrium and several pacing/sensing sites in one or more ventricles. Each intrinsic and each paced event in each of these sites may introduce one or more unwanted potentials in cardiac signals associated with the pacing/sensing sites. Each unwanted potential may have a relatively fixed temporal relationship with at least one intrinsic or paced event in one of the sites. Because whether such unwanted potentials will be present for an individual patient and how they are temporally related to any of the intrinsic and paced events are not necessarily known before device implantation, applying a programmable blanking period, as suggested by Routh et al., will require numerous blanking refractory periods. The number of such blanking or refractory periods will grow exponentially with the number of pacing/sensing sites in a multiple site pacing system, eventually to a point that requires a system size that cannot be accommodated by an implantable device and, moreover, this causes significant difficulties and potential for confusion to the physician programming the implantable device. What is, therefore, needed is one or more blanking or refractory periods that do not require excessive system resources and which are easy to program by a physician who observes the cardiac signals during or after a device implantation. The present invention meets these and other needs that will become apparent from a review of the description of the present invention.

SUMMARY OF THE INVENTION

The present invention includes programmable refractory or blanking periods and floating refractory or floating blanking periods, which are incorporated within the sensing protocol for each selected cycle, thereby increasing the time period for normal sensing. The floating refractory period is initiated by a predetermined (preprogrammed) triggering event and may be retriggerable if a triggering event is detected during the floating refractory period.

The present invention provides a single- or multi-chamber cardiac rhythm management device having multiple pacing electrodes positioned at a plurality of sites within selected chamber(s) of the heart. The cardiac rhythm management device of the present invention stimulates the heart in a pre-selected stimulation mode, and increases the time period during a selected cardiac cycle for normal sensing. The cardiac rhythm management device of the present invention includes a power supply, a controller, circuitry for sensing intrinsic cardiac events, timing circuitry, a predefined sensing protocol, and circuitry for determining and generating stimulation pulses. The controller and circuitry for sensing are capable of detecting and identifying atrial and/or ventricular events and transmitting signals containing information corresponding to these sensed events. The transmitted signals may be utilized by the controller, for example and without limitation, to thereafter track, over time, the sensed events. The controller also utilizes the timing and sensing circuitry for determining and generating stimulation pulses to selectively stimulate pre-selected chambers of the patient's heart.

As described below in greater detail, in the preferred embodiment, the controller initiates one or more floating refractory or blanking periods that may follow a shortened "conventional" programmed refractory or blanking period. The floating refractory or blanking periods are initiated by predefined or programmed triggering events. Those skilled in the art will appreciate that the floating refractory or blanking period may be implemented in fixed hardware and/or software of the device. The floating refractory period may be fixed in duration or may be retriggerable if a triggering event occurs during the floating refractory period. Also, if a triggering event occurs during the floating refractory or blanking period, the event may be detected and "marked" by the device, with the pacing logic ignoring the event. The triggering event for the floating refractory period may be defined, for example, by an arbitrary pace, sense, and/or timing interval expiration event. The floating refractory period may be associated with one or more device channels, and one triggering event can simultaneously trigger floating refractory periods for one or more or a combination of other device sensing channels.

In one embodiment of the present invention, the sensing protocol utilized by the controller includes a first and a second refractory period for sensed events in pre-selected chambers during the cardiac cycle. The controller may initiate first and second refractory periods associated with the ventricles, dependent upon events occurring in the atrium. A time gap is provided for between the first and second refractory periods. Alternatively, the controller may initiate first and second refractory periods associated with the atrium, dependent upon events occurring in the ventricles. Further, the second refractory period may be initiated by an event sensed in an atrial channel and this refractory period may apply to the same and/or different atrial channel. Likewise, the second refractory period may be initiated by an event sensed in a ventricular channel and this refractory period may apply to the same and/or different ventricular channel.

The controller may be implemented in any of several forms, including a dedicated state device or a microprocessor with code, and may include Read Only Memory (ROM) for storing programs to be executed by the controller and Random Access Memory (RAM) for storing operands used in carrying out the computations by the controller. The controller is electrically coupled to the power supply and manipulates the electrical circuitry for the sensing and tracking and the circuitry for determining and generating stimulation pulses, during each cardiac cycle. The predefined sensing protocol may be stored in the controller and is utilized by the controller to increase the time period during a cardiac cycle for normal sensing of intrinsic events.

The circuitry for sensing includes one or more channels for sensing events associated with the atrium and/or one or more channels for sensing events associated with the ventricles. The controller, in accordance with a preset sensing protocol, manipulates the sensing channels to create, for example, the first and second refractory periods. Without limitation, the controller may blank a portion of the signal sensed from either the atrium or ventricles that is sensed during the second refractory period, thereby potentially inhibiting a response in accordance with the pacing logic. The second or floating refractory period may be initiated a predetermined amount of time after the end of the first refractory period. Alternatively, the second refractory period may be initiated automatically if intrinsic conduction from the atrium is sensed. In another alternative embodiment, the second refractory period may be initiated automatically if intrinsic conduction from the ventricle is sensed.

In use, the cardiac rhythm management device of the present invention may be utilized to stimulate pre-selected chambers of a patient's heart in accordance with a predefined stimulation sequence. The present invention provides a method for assisting a physician in avoiding an unwanted potential by first identifying the unwanted potential by observing all of the cardiac signals sensed from different sites in the heart and then ascertaining a temporal relationship between the unwanted potential and a known, repeatable intrinsic or paced event. The device is then programmed with the known repeatable intrinsic or paced event employed as a trigger event that triggers a blanking or refractory period. A sensing channel where the unwanted potential is identified is then programmed as the channel to which the blanking or refractory period is to be applied. Further, a delay value is programmed that starts with the trigger event and that extends to a point in time before which the unwanted potential is believed not to occur. Finally, a duration of the blanking or refractory period that starts with the end of the delay and extends to cover a period of time during which the unwanted potential is believed to have occurred is programmed.

It is accordingly a principal object of the present invention to provide an enhanced blanking or refractory period that reduces the likelihood of failure to identify intrinsic events.

Another object of the present invention is to provide a rhythm management device having a sensing protocol that avoids misidentification of artifacts and evoked potentials while enhancing the ability of the device to sense intrinsic events by increasing the time period for normal sensing.

Still another object of the present invention is to provide a cardiac rhythm management device that increases the ability of the device to detect tachyarrhythmias.

Yet another object of the present invention is to provide a cardiac rhythm management device that may include separate refractory and floating refractory periods for each selected cardiac cycle which may be utilized to increase the time period for normal sensing.

These and other objects and advantages of the present invention will become readily apparent to those skilled in the art from a review of the following detailed description of the invention especially when considered in conjunction with the claims and accompanying drawings in which like numerals in the several views refer to corresponding parts.

DETAILED DESCRIPTION OF THE INVENTION

Figure 1:
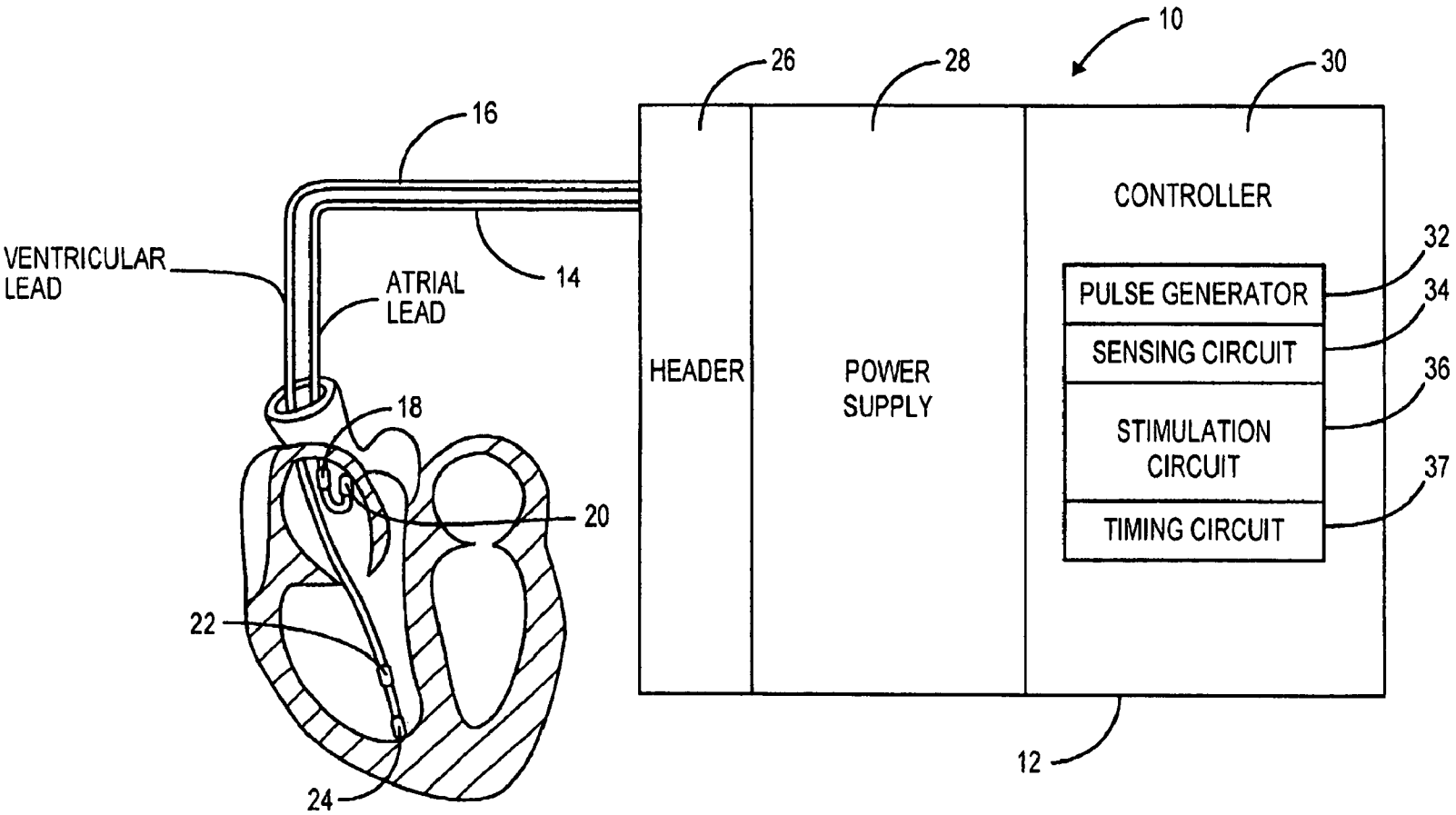
FIG. 1 is a block diagram depicting a cardiac rhythm management device in accordance with the present invention.

The present invention represents broadly applicable improvements to the sensing protocol of a cardiac rhythm management device. The embodiments detailed herein are intended to be taken as representative or exemplary of those in which the improvements of the invention may be incorporated and are not intended to be limiting. Referring first to FIG. 1, the cardiac rhythm management device 10 of the present invention is shown including a housing 12, atrial lead 14, and ventricular lead 16. The distal end of the atrial lead shown positioned in the right atrium includes electrodes 18 and 20. The distal end of the ventricular lead 16 shown positioned in the right ventricle includes ventricular electrodes 22 and 24. The atrial lead 14 and ventricular lead 16 are engaged to header 26 affixed to the housing and may be electrically coupled to the power supply 28 and controller 30 contained within the housing 12 in a known fashion. It should be appreciated that other lead configurations of known construction may be utilized, dependent upon the particular desired stimulation and particular placement of the lead. Without limitation, the controller 30 includes a pulse generator 32, sensing circuit 34, stimulation circuit 36 and timing circuit 37. The pulse generator 32, sensing circuit 34, stimulation circuits 36, and timing circuit 37 of known construction may be modified to include the sensing protocol of the present invention as described below in greater detail. In particular, the refractory/blanking periods may be implemented in hardware and/or software in a known manner.

Figure 2:
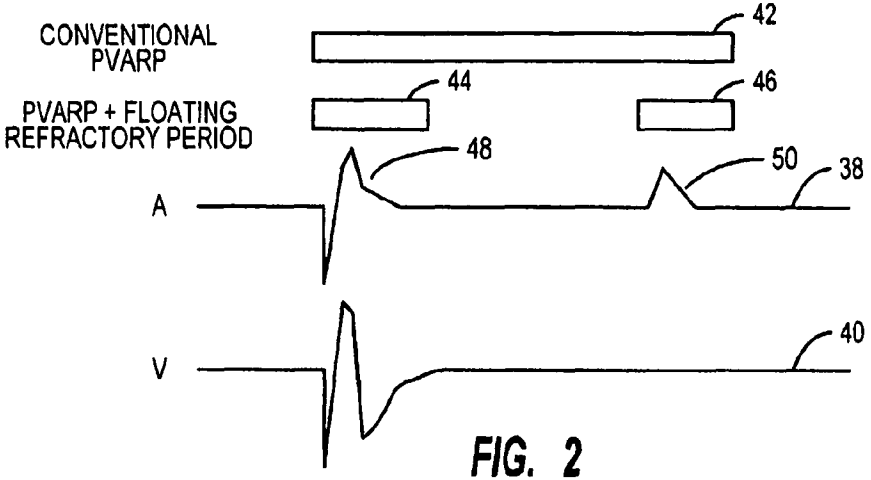
FIG. 2 is a plot showing retrograde conduction sensed by an atrial sensing channel of the sensing circuit and associated refractory and floating refractory periods in comparison with a conventional Post Ventricular Atrial Refractory Period.

Referring next to FIG. 2, one embodiment of the sensing protocol which utilizes a refractory period 44 and floating refractory period 46 is shown. In this embodiment, electrogram signals 38 and 40 are sensed over time by respective atrial and ventricular sensing channels comprising sensing circuit 34 in FIG. 1. The sensing protocol initiates a first refractory period 44 having a predetermined duration and then later initiates a floating refractory period 46 also having a predetermined duration. The initiation of the first refractory period 44 and the floating refractory period is dependent upon the timing of sensed signals exceeding a predetermined threshold. The floating refractory period 46 is initiated a preset time following a triggering event and lasts for a predetermined amount of time. The floating refractory period 46 is used in combination with the first refractory period 44 to increase the time available for normal sensing.

In the embodiment shown in FIG. 2, the triggering event is defined by the expiration of a predetermined timing interval. It should be appreciated that the triggering event is programmable and may alternately include for example, without limitation, a paced event or a sensed event in either the atrium or ventricles. Further, the floating/blanking or refractory period may be implemented in a sensing protocol for either the atrium or ventricles. Also, the amount of time required for the refractory period 44 and floating refractory period 46 may be varied through physician programming, depending upon the particular patient's needs.

As further seen in FIG. 2, following a ventricular pace or ventricular intrinsic event the atrial electrogram 38 includes a potential artifact 48 later followed by a retrograde conducted P-wave 50 occurring several milliseconds after the end of the sensed potential artifact and the end of the sensed ventricular event. The refractory period 44 and floating refractory period 46 blank the sensing circuit 34 from reacting to the artifact 48 and retrograde P-wave 50, but allows for sensing events occurring between the artifact 48 and retrograde 50, thus maximizing the time available for normal sensing. This increased time for sensing may be particularly relevant in treating CHF patients having conduction defects, since artifacts and/or evoked potentials may occur a significantly longer time after the triggering event (thereby requiring an especially long PVARP) than experienced by patients having normal conduction times. Further, in left ventricular pacing of a CHF patient, when the lead is in a uni-polar configuration and placed near the base of the ventricle, signals associated with left atrium activity may also be sensed by the left ventricular lead. Those skilled in the art will appreciate that the floating/blanking refractory period 46 may be used to blank signals corresponding to the left atrial P-wave with minimum interruption of left ventricular sensing.

In bi-ventricular or other multi-site pacing, additional artifact and evoked potentials are expected which consequently require longer refractory periods, thereby further reducing the normal sensing time. For example, in the case of bi-ventricular pacing, the ventricular refractory period must be long enough to blank out far-field sensing and/or retrograde conduction from both the right ventricle and the left ventricle. These long ventricular refractory periods may be required to prevent the right ventricular channel from sensing left ventricular activities and vice versa. The floating blanking refractory/period will extend the normal sensing time and may also be implemented in other multi-channel stimulation configurations, ensuring successful implementation of brady and tachy therapy algorithms by maximizing the normal sensing time.

Figure 3:
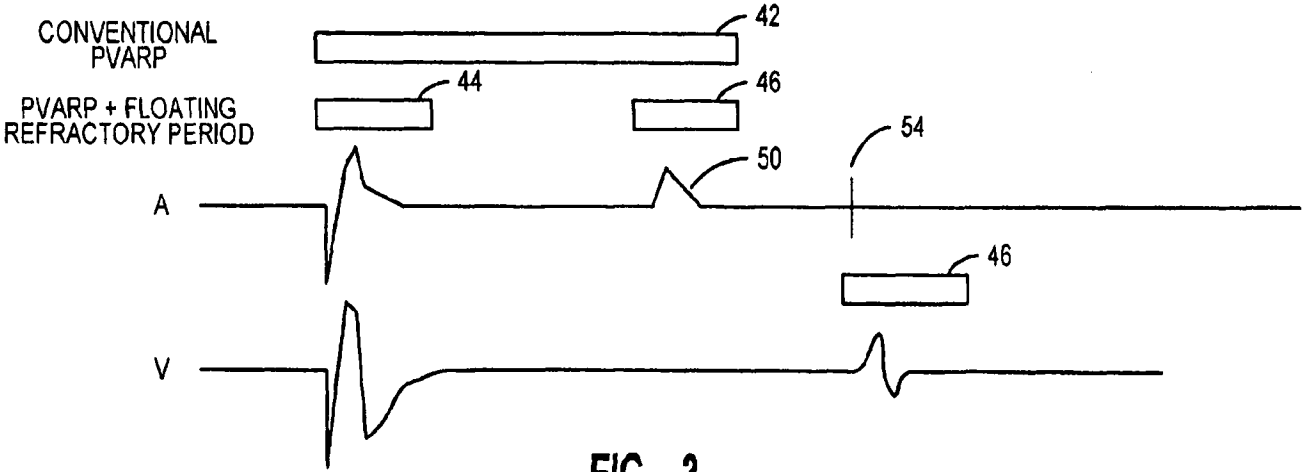
FIG. 3 is a plot showing an intrinsic event sensed by the atrial and ventricular sensing channels of the sensing circuit and associated refractory and floating refractory periods in conjunction with atrial stimulation and associated ventricular refractory and floating refractory periods.

FIG. 3 illustrates refractory and floating refractory periods, 44 and 46 respectively, in both the atrial and ventricular channels when pacing 54 occurs in the atrium. A pacing event is identified by numeral 54 in FIG. 3. In this embodiment, the triggering event for the floating refractory period 46' in the ventricular channel is a paced event 54 in the atrium. Implementing refractory and floating refractory periods for each sensing channel increases the total time for normal sensing.

Figure 4:
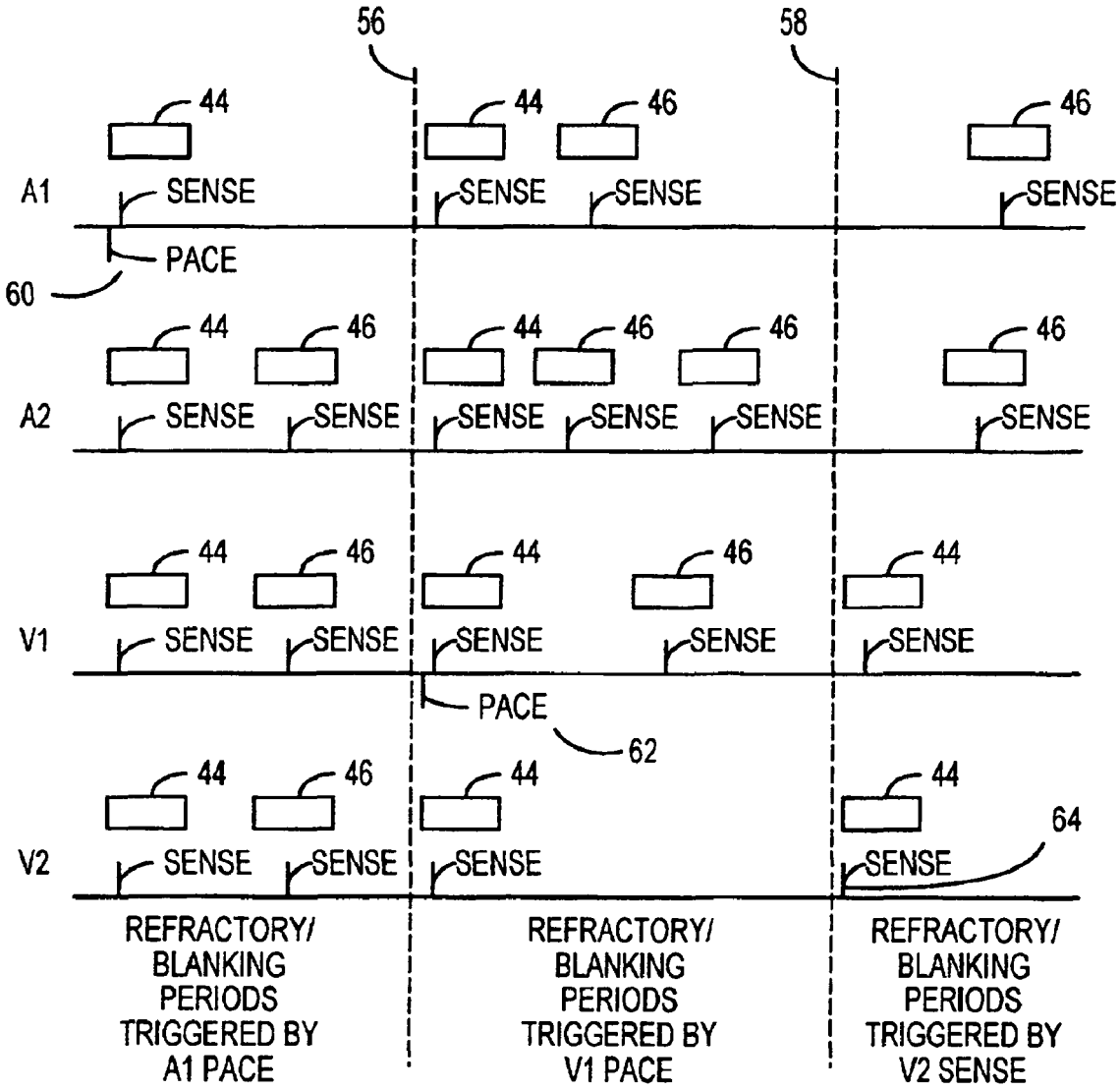
FIG. 4 is a plot showing several pacing and intrinsic events in relation to the timing and occurrence of a first refractory and second refractory or floating refractory/blanking period.

FIG. 4 illustrates implementation of refractory and floating refractory periods 44 and 46 respectively for multiple sensing channels identified as A1, A2, V1, and V2, wherein the floating refractory periods 46 are triggered by paced and intrinsic events. Three pacing/sensing sequences divided by dotted vertical lines 56 and 58 may each occur independently. Although the pacing/sensing sequences are shown sequentially, the representation should not be construed as sequentially limited, but, rather, those skilled in the art will appreciate that each sequence may occur independently of the other. With reference to the first of the three pacing/sensing sequences, a pacing stimulus 60 is delivered to an atrium associated with sensing channel A1. A refractory period 44 is initiated in each channel A1, A2, V1, and V2 at the time the pacing stimulus 60 is delivered. A floating refractory period 46 is initiated for each sensing channel A2, V1, and V2. As illustrated, the floating refractory period 46 may blank sensed events occurring during the refractory period. Referring to the next pacing/sensing sequence shown in FIG. 4, a pacing stimulus 62 is delivered to a ventricle associated with the sensing channel V1. A refractory period 44 is initiated on each channel A1, A2, V1, and V2 at the time the pacing stimulus 62 is delivered. A floating refractory period 46 is then initiated for each sensing channel A1, A2, and V1. A subsequent event sensed in channel V1 triggers a floating refractory period 46 in channel A2. The third pacing/sensing sequence shown in FIG. 4 shows an intrinsic event 64 sensed by channel V2 which initiates a refractory period 44 in channels V1 and V2. Floating refractory periods 46 are initiated in channels A1 and A2 which blanks sensing of intrinsic events detected in channels A1 and A2.

Figure 5:
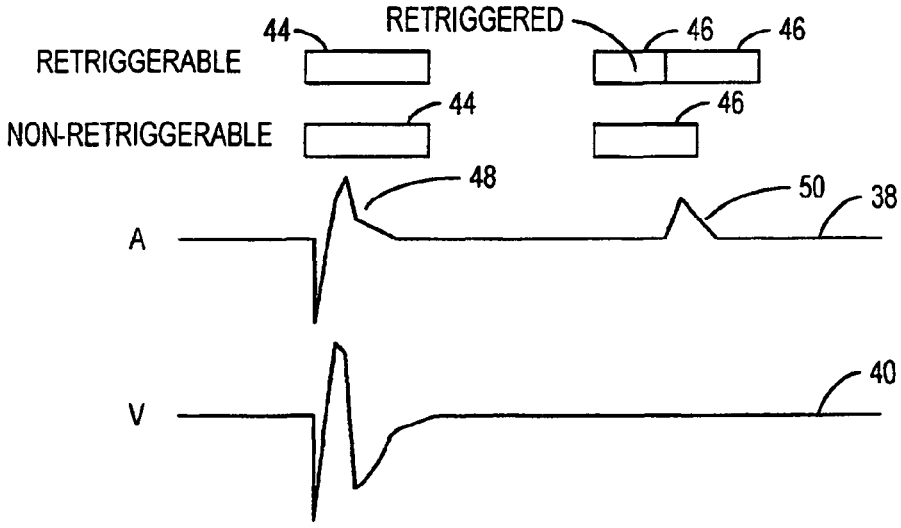
FIG. 5 is a plot showing retrograde conduction sensed by an atrial sensing channel of the sensing circuit and an associated non-retriggerable floating refractory period and a retriggerable floating refractory period shown for comparison.

The start and duration of the floating refractory period 46 for a given sensing channel may also be programmed as a function of the heart rate or pacing rate. Also, the floating refractory period may be programmed to restart upon occurrence of a triggering event during floating refractory period (see FIG. 5).

Figure 6:
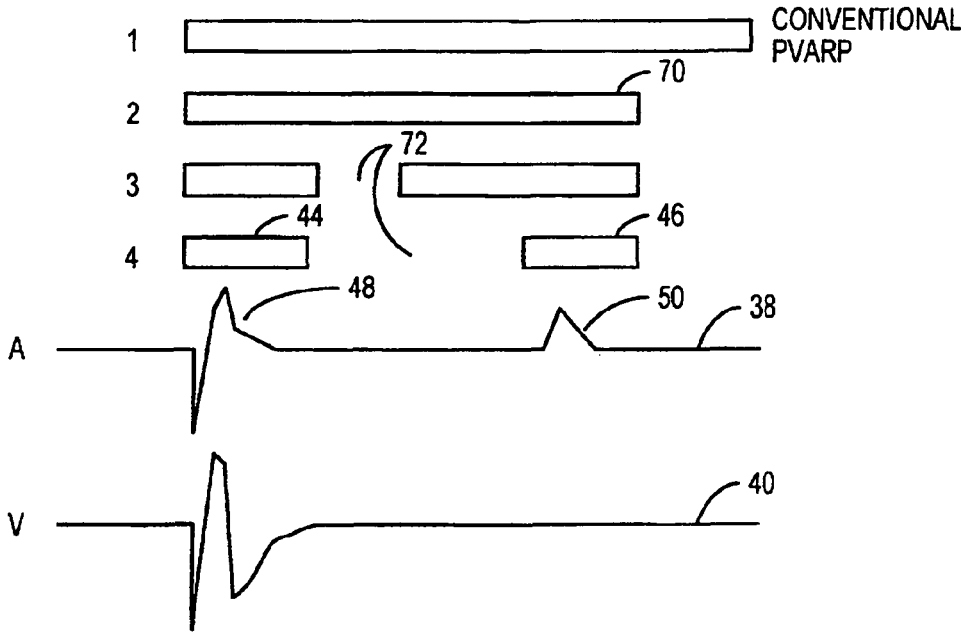
FIG. 6 shows a progression of modifications to the conventional refractory period to derive a preferred first shortened "conventional" refractory period and a second floating refractory period, which may be utilized to automatically program the refractory and floating refractory periods.

In use, under certain circumstances the timing and duration of the floating refractory period may be automated. For example, with reference to FIG. 6, the device may start by using a maximum conventional refractory period (PVARP). The refractory period is then shortened to the minimum conventional refractory period 70. A window 72 in the shortened conventional PVARP is created and then the window 72 is extended or maximized.

Alternatively, the device may gradually shorten the refractory period until a potential is sensed. The duration for the first refractory period may then be defined a predetermined amount greater than the elapsed time until the potential was sensed. A window of time that "interrupts" a conventional refractory period may expand from the end of the first refractory period to cover the time during which nothing is sensed. As described above, this window may expand by a predefined amount, may terminate when a pace occurs or when an intrinsic event is sensed. As recognized above, the various embodiments of this invention include using one or more floating blanking/refractory periods in a pacemaker, defibrillator, CHF device, and/or atrial fibrillation devices or any other device whose logic and timing depend on sensing events. Use of the first refractory and floating refractory periods maximizes the normal sensing time for each sensing channel. Those skilled in the art will appreciate that the procedure for automatically implementing the floating refractory period may also be utilized manually by a programmer.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device capable of detecting intrinsic depolarization events, comprising:

a pulse generator for selectively stimulating a plurality of sites in at least one chamber of a patient's heart;

a sensing circuit configured to receive signals indicative of the depolarization events from a first electrode positioned within a sensing channel for an atrium of the patient's heart and a second electrode positioned within a sensing channel for a ventricle of the patient's heart; and a controller configured to receive data from the sensing circuit and to control the pulse generator, wherein the controller prevents the use of data to detect intrinsic depolarization events during a plurality of programmable refractory periods in timed relation relative to a sensed triggering event [in] *programmably selected from* one of a plurality of programmably selectable sensing channels.

2. The cardiac rhythm management device, *as* in claim 1, wherein one of the plurality of refractory periods is a floating refractory period that may selectively be applied to said at least one sensing channel for the atrium and said at least one sensing channel for the ventricle.

3. The cardiac rhythm management device, as in claim 1, wherein at least one of the programmable refractory periods is initiated a predetermined amount of time after the end of a first refractory period, the first refractory period being initiated coincidental with sensing an intrinsic event.

4. The cardiac rhythm management device, as in claim 1, wherein at least one of the programmable refractory periods is triggered by a stimulation of a pre-selected chamber of the heart.

5. The cardiac rhythm management device, as in claim 1, wherein the triggering event is a sensed intrinsic event.

6. The cardiac rhythm management device, as in claim 1, wherein the triggering event includes a paced event.

7. The cardiac rhythm management device, as in claim 1, wherein the triggering event includes an intrinsic atrial event.

8. The cardiac rhythm management device, as in claim 1, wherein the triggering event includes an intrinsic ventricular event.

9. The cardiac rhythm management device, as in claim 1, wherein the triggering event includes a paced atrial event.

10. The cardiac rhythm management device[of], *as in* claim 1, wherein the triggering event includes a paced ventricular event.

11. The cardiac rhythm management device, as in claim 1, wherein preprogrammed sensed triggering events from the atrium are blanked during a floating refractory period.

12. The cardiac rhythm management device, as in claim 1, wherein preprogrammed sensed triggering events from the ventricle are blanked during a floating refractory period.

13. The cardiac rhythm management device, as in either claim 11 or claim 12, wherein the floating refractory period is retriggerable.

14. The cardiac rhythm management device, as in claim 1, wherein the controller initiates first and second refractory periods associated with the ventricle dependent upon sensed triggering events occurring in the atrium.

15. The cardiac rhythm management device, as in claim 1, wherein the controller initiates first and second refractory periods associated with the atrium dependent upon sensed triggering events occurring in the ventricle.

16. A multi-chamber cardiac rhythm management device functioning in a pre-selected stimulation mode and capable of atrial and ventricular tracking, said device comprising:

sensing means for sensing at least one of atrial and ventricular events and transmitting signals containing information corresponding to sensed events;

stimulation means for selectively stimulating pre-selected chambers of the patient's heart; and a programmable controller coupled to said means for sensing and said stimulation means, wherein during a cardiac cycle said controller manipulates the means for sensing to thereby create [a] first and second refractory [period] *periods* of sensed events for programmably [pre-selected chambers] *selected sites in the patient's heart* during the cardiac cycle, *wherein the programmably selected sites are programmably selected for applying the first and second refractory periods thereto*.

17. The cardiac rhythm management device as recited in claim [15] *16*, wherein the second refractory period is initiated a predetermined amount of time after the end of the first refractory period.

[18. The cardiac rhythm management device as recited in claim 15, wherein the second refractory period is initiated a predetermined amount of time after the end of the first refractory period.]

19. The cardiac rhythm management device as recited in claim [15] *16*, wherein the controller is programmed such that the second refractory period is initiated if intrinsic events from the atrium are sensed.

20. The cardiac rhythm management device as recited in claim [15] *16*, wherein the controller is programmed such that the second refractory period is initiated if intrinsic events from the ventricle are sensed.

21. The cardiac rhythm management device as recited in claim [15] *16*, wherein sensed events from the atrium are blanked during the second refractory period.

22. The cardiac rhythm management device as recited in claim [15] *16*, wherein sensed events from the ventricles are blanked during the second refractory period.

23. The cardiac rhythm management device as recited in claim [15] *16*, wherein the controller initiates first and second refractory periods associated with the ventricles dependent upon events occurring in the atrium.

24. The cardiac rhythm management device as recited in claim [15] *16*, wherein the controller initiates first and second refractory periods associated with the atrium dependent upon events occurring in the ventricle.

25. A cardiac rhythm management device capable of unipolar or bipolar atrial and ventricular stimulation, said cardiac rhythm management device including:

[(a)] a controller;

[(b)] means for stimulating at least one of an atrium or ventricle of a heart, said means being electrically coupled to said controller;

[(c)] sensing means for sensing a cardiac electrogram, said sensing means electrically coupled to the controller;

[(d)] an atrial lead having an atrial electrode electrically coupled to the controller;

[(e)] a ventricular lead having a ventricular electrode electrically coupled to the controller; and

[(f)] said controller having means for defining a refractory period and a floating refractory period for a predetermined cardiac cycle for a [programmable] *programmably* selectable chamber of the heart *that is programmably selectable for applying the refractory period and the floating refractory period thereto*.

26. The cardiac rhythm management device recited in claim 25, wherein the sensing means includes a programmably designate sensing channel for the atrium and a programmably designated sensing channel of the ventricle wherein the controller selects the sensing channel in creating the refractory period and floating refractory period.

27. The cardiac rhythm management device as recited in claim 25, wherein the floating refractory period is initiated a preprogrammed amount of time after the end of the refractory period.

[28. The cardiac rhythm management device as recited in claim 26, wherein the floating refractory period is initiated a preprogrammed amount of time after the end of the refractory period.]

29. The cardiac rhythm management device as recited in claim 25, wherein the floating refractory period is initiated if intrinsic events from the atrium are sensed.

30. The cardiac rhythm management device as recited in claim 25, wherein the floating refractory period is initiated if intrinsic events from the ventricle are sensed.

31. The cardiac rhythm management device as recited in claim 25, wherein sensed events from the atrium are blanked during the floating refractory period.

32. The cardiac rhythm management device as recited in claim 25, wherein sensed events from the ventricles are blanked during the floating refractory period.

33. The cardiac rhythm management device as recited in claim 25, wherein the controller initiates a refractory period and floating refractory period associated with the ventricles dependent upon preprogrammed triggering vents occurring in the atrium.

34. The cardiac rhythm management device as recited in claim 25, wherein the controller initiates a refractory period and floating refractory period associated with the atrium dependent upon preprogrammed triggering events occurring in the ventricles.

35. The cardiac rhythm management device as in any one of claims 25-34 wherein the floating refractory period is retriggerable.

36. A method for stimulating a pre-selected chamber of a patient's heart using a cardiac rhythm management device of the type which senses and determines independently atrial and ventricular depolarization events and includes a plurality of programmed timing and stimulation intervals, said method comprising the steps of:

[a)] sensing cardiac electrograms and detecting an intrinsic events occurring in pre-selected chambers of the patient's heart; then

[b)] identifying [a time] *times* at which *unwanted potentials of* the intrinsic events are sensed;

[c)] initiating a first interval for blanking detected events for a first predetermined portion of a cardiac cycle;

[d)] initiating a second interval for blanking detected events for a second predetermined portion of the cardiac cycle; [and]

*programming a sensing channel to which the first interval and the second interval are applied;*

*programming timing of the second interval using the identified times; and*

[e)] stimulating pre-selected chambers in accordance with a predetermined stimulation protocol so long as an intrinsic cardiac event having an amplitude exceeding a predetermined amount is not [sense] *sensed* between the first and second intervals.

37. The method as recited in claim 36, wherein the second interval is initiated a predetermined amount of time after an end of the first interval.

38. The method as recited in claim 36, wherein the second interval is initiated when an intrinsic event from the atrium is sensed.

39. The method as recited in claim 36, wherein the second interval is initiated when an intrinsic event from the ventricle is sensed.

40. The method as recited in claim 36 wherein the blanked event is associated with the atriums.

41. The method as recited in claim 36, wherein the blanked event is associated with the ventricle.

42. A method for programming a cardiac rhythm management device to enhance its ability to sense intrinsic depolarization events while avoiding detection of artifacts and after-potentials comprising[the step of]:

[(a)] examining cardiac electrogram data originating from programmably selectable sites in a heart to identify unwanted potentials;

[(b)] determining a temporal relationship between the unwanted potentials and a known, repeatable, intrinsic or paced event;

[(c)] programming the known, repeatable, intrinsic or paced event as a trigger event that initiates a blanking or refractory period in a sensing channel exhibiting the unwanted potential;

[(d)] programming a delay value that starts with the trigger event and extends to a point in time before which the unwanted potential is predicted not to occur; and

[(e)] programming a duration of the blanking or refractory period that begins with the end of the delay value and extends to cover a period of time during which the unwanted potential is predicted to occur.

43. The cardiac rhythm management device as in any one [claim 16 or 17-24] *of claims 16, 17 and 19-24* wherein the second refractory period is retriggerable.

*44. A cardiac rhythm management device capable of detecting intrinsic depolarization events, comprising:*

*a sensing circuit configured to receive signals indicative of the depolarization events from a first electrode positioned within a sensing channel for an atrium of a patient's heart and a second electrode positioned within a sensing channel for a ventricle of the patient's heart; and*

*a controller configured to receive data from the sensing circuit and prevent use of data to detect intrinsic depolarization events during one or more programmable refractory periods in timed relation relative to a sensed triggering event programmably selected from one of a plurality of sensing channels.*

*45. The cardiac rhythm management device, as in claim 44, wherein one of the one or more programmable refractory periods is a floating refractory period that is initiated a programmable amount of time after the end of a first refractory period, the first refractory period being initiated coincidental with the sensed triggering event.*

*46. The cardiac rhythm management device, as in claim 44, comprising a pulse generator configurable to selectively stimulate a plurality of sites in at least one chamber of the patient's heart, and wherein the controller is configured to control the pulse generator and prevent the use of data to detect intrinsic depolarization events during the plurality of programmable refractory periods in controlling the pulse generator.*

*47. The cardiac rhythm management device, as in claim 46, wherein at least one of the programmable refractory periods is triggered by a stimulation of a pre-selected chamber of the heart.*

*48. The cardiac rhythm management device, as in claim 46, wherein the triggering event is a sensed intrinsic event.*

*49. The cardiac rhythm management device, as in claim 46, wherein the triggering event includes a paced event.*

*50. The cardiac rhythm management device, as in claim 46, wherein the triggering event includes an intrinsic atrial event.*

*51. The cardiac rhythm management device, as in claim 46, wherein the triggering event includes an intrinsic ventricular event.*

*52. The cardiac rhythm management device, as in claim 46, wherein the triggering event includes a paced atrial event.*

*53. The cardiac rhythm management device, as in claim 46, wherein the triggering event includes a paced ventricular event.*

*54. The cardiac rhythm management device, as in claim 45, wherein preprogrammed sensed triggering events from the atrium are blanked during the floating refractory period.*

*55. The cardiac rhythm management device, as in claim 45, wherein preprogrammed sensed triggering events from the ventricle are blanked during the floating refractory period.*

*56. The cardiac rhythm management device as in any one of claims 45, 54, and 55, wherein the floating refractory period is retriggerable.*

*57. The cardiac rhythm management device, as in claim 46, wherein the controller initiates first and second refractory periods associated with the ventricle dependent upon sensed triggering events occurring in the atrium.*

*58. The cardiac rhythm management device, as in claim 46, wherein the controller initiates first and second refractory periods associated with the atrium dependent upon sensed triggering events occurring in the ventricle.*

*59. A cardiac rhythm management device, comprising:*

*a controller;*

*sensing means for sensing a cardiac electrogram, said sensing means electrically coupled to the controller;*

*an atrial lead having an atrial electrode electrically coupled to the controller;*

*a ventricular lead having a ventricular electrode electrically coupled to the controller; and*

*said controller having means for defining a refractory period and a floating refractory period in a cardiac cycle for a programmably selectable site in a heart, wherein the programmably selectable site is programmably selectable for applying the refractory period and the floating refractory period thereto.*

*60. The cardiac rhythm management device as recited in claim 59, wherein the sensing means includes a programmably designated sensing channel for the atrium and a programmably designated sensing channel for the ventricle wherein the controller selects the sensing channel in creating the refractory period and floating refractory period.*

*61. The cardiac rhythm management device as recited in claim 59, wherein the floating refractory period is initiated a preprogrammed amount of time after the end of the refractory period.*

*62. The cardiac rhythm management device as recited in claim 59, wherein the floating refractory period is initiated if intrinsic events from the atrium are sensed.*

*63. The cardiac rhythm management device as recited in claim 59, wherein the floating refractory period is initiated if intrinsic events from the ventricle are sensed.*

*64. The cardiac rhythm management device as recited in claim 59, wherein sensed events from the atrium are blanked during the floating refractory period.*

*65. The cardiac rhythm management device as recited in claim 59, wherein sensed events from the ventricles are blanked during the floating refractory period.*

*66. The cardiac rhythm management device as recited in claim 59, wherein the controller initiates a refractory period and floating refractory period associated with the ventricles dependent upon preprogrammed triggering events occurring in the atrium.*

*67. The cardiac rhythm management device as recited in claim 59, wherein the controller initiates a refractory period and floating refractory period associated with the atrium dependent upon preprogrammed triggering events occurring in the ventricles.*

*68. The cardiac rhythm management device as recited in any one of claims 59-67 wherein the floating refractory period is retriggerable.*

*69. A cardiac rhythm management device capable of detecting intrinsic depolarization events, comprising:*

*a pulse generator for selectively stimulating a plurality of sites in at least one chamber of a patient's heart;*

*a sensing circuit configured to receive signals indicative of the depolarization events from a first electrode positioned within a sensing channel for an atrium of the patient's heart and a second electrode positioned within a sensing channel for a ventricle of the patient's heart; and*

*a controller configured to receive data from the sensing circuit and to control the pulse generator, wherein the controller prevents the use of data to detect intrinsic depolarization events during a plurality of programmable refractory periods in timed relation relative to a sensed triggering event programmably selected from one of a plurality of programmably selectable sensing channels, wherein at least one of the programmable refractory periods is initiated a predetermined amount of time after the end of a first refractory period, the first refractory period being initiated coincidental with sensing an intrinsic event.*

*70. A multi-chamber cardiac rhythm management device functioning in a pre-selected stimulation mode and capable of atrial and ventricular tracking, said device comprising:*

*sensing means for sensing at least one of atrial and ventricular events and transmitting signals containing information corresponding to sensed events;*

*stimulation means for selectively stimulating pre-selected chambers of a patient's heart; and*

*a programmable controller coupled to said means for sensing and said stimulation means, wherein during a cardiac cycle said controller manipulates the means for sensing to thereby create first and second refractory periods of sensed events for programmably pre-selected chambers of the patient's heart during the cardiac cycle, wherein the second refractory period is initiated a predetermined amount of time after the end of the first refractory period.*

*71. A cardiac rhythm management device capable of detecting intrinsic depolarization events, comprising:*

*a sensing circuit configured to receive signals indicative of the depolarization events from a first electrode positioned within a sensing channel for an atrium of a patient's heart and a second electrode positioned within a sensing channel for a ventricle of the patient's heart; and*

*a controller configured to receive data from the sensing circuit and prevent use of data to detect intrinsic depolarization events during one or more programmable refractory periods in timed relation relative to a sensed triggering event programmably selected from one of a plurality of sensing channels, wherein one of the one or more programmable refractory periods is a floating refractory period that is initiated a programmable amount of time after the end of a first refractory period, the first refractory period being initiated coincidental with the sensed triggering event.*

*72. A cardiac rhythm management device, comprising:*

*a controller;*

*sensing means for sensing a cardiac electrogram, said sensing means electrically coupled to the controller;*

*an atrial lead having an atrial electrode electrically coupled to the controller;*

*a ventricular lead having a ventricular electrode electrically coupled to the controller; and*

*said controller having means for defining a refractory period and a floating refractory period in a cardiac cycle for a programmably selectable site in a heart, wherein the floating refractory period is initiated a preprogrammed amount of time after the end of the refractory period.*

* * * * *

UNITED STATES PATENT AND TRADEMARK OFFICE

CERTIFICATE OF CORRECTION

PATENT NO. : RE42,933 E
APPLICATION NO. : 11/900901
DATED : November 15, 2011
INVENTOR(S) : Zhengnian Tang et al.

It is certified that error appears in the above-identified patent and that said Letters Patent is hereby corrected as shown below:

In column 9, line 25, in Claim 16, delete “the” and insert -- a --, therefor.

In column 10, line 2, in Claim 25, after “or” insert -- a --.

In column 10, line 47, in Claim 33, delete “vents” and insert -- events --, therefor.

In column 10, line 63, in Claim 36, after “detecting” delete “an”.

In column 11, line 50, in Claim 43, delete “17” and insert -- 17, --, therefor.

Signed and Sealed this
Thirty-first Day of January, 2012

David J. Kappos

David J. Kappos
*Director of the United States Patent and Trademark Office*